United States Patent [19]

Sachse

[11] Patent Number: 4,487,202
[45] Date of Patent: Dec. 11, 1984

[54] TESTIS SUPPORT FOR ELEVATING AND TREATING DISEASED TESTES AND EPIDIDYMIDES

[76] Inventor: Hans Sachse, Lerchenstr. 55, 85 Nurnberg GO, Fed. Rep. of Germany

[21] Appl. No.: 471,775

[22] Filed: Mar. 3, 1983

[30] Foreign Application Priority Data

Mar. 16, 1982 [DE] Fed. Rep. of Germany ....... 3209427

[51] Int. Cl.³ .............................................. A61F 5/40
[52] U.S. Cl. ................................................... 128/158
[58] Field of Search ........................................ 128/158

[56] References Cited

U.S. PATENT DOCUMENTS 1,074,147  9/1913  Whitlock ............................. 128/158
1,474,927 11/1923  Cawthra ............................. 128/158

Primary Examiner—John D. Yasko
Attorney, Agent, or Firm—Keil & Weinkauf

[57] ABSTRACT

In order to elevate and treat diseased testes and epididymides of a recumbent man, they must, for medical treatment, be lifted above the level of the thighs by a testis support. The testis support indicated for this purpose has, in its longitudinal axis, a slight V-shaped deviation from planarity so that its wings lie on and lightly grip the two thighs of the recumbent man. A recess to receive the attachment of the scrotum is present in the V notch on one longitudinal edge. The support is composed of rigid, partially rigid or completely elastic soft material.

7 Claims, 4 Drawing Figures

TESTIS SUPPORT FOR ELEVATING AND TREATING DISEASED TESTES AND EPIDIDYMIDES

Applicant hereby claims priority from his German patent application No. P3209427.2 filed Mar. 16, 1982 under 35 USC 119.

The invention relates to a testis support for elevating and treating diseased testes and epididymides of a recumbent man in order to lift the testes above the level of the thigh.

It has hitherto been customary to elevate the scrotum for medical treatment by placing a coil of paper or fabric underneath. However, this has the disadvantage that every movement of the patient changes the position of the coil and leads to an incorrect position of the scrotum. This can lead, particularly in elderly patients, to the coil being lost somewhere in the bed after a short time.

The other method which has hitherto been tried comprises stretching a cloth from one thigh to the other with strips of plaster and the scrotum being rested on this. This is also an unsatisfactory method, since in this method the diseased scrotum, which is usually very heavy, easly slips back down through the gap between the stretched cloth and the body.

Thus, the invention is based on the object of producing a testis support for treating and elevating diseased testes and epididymides which avoids the disadvantages of known designs.

This object is achieved according to the invention by a plane support which has, in its longitudinal axis, a slight V-shaped deviation from planarity so that it lies on, and lightly grips, both thighs of the recumbent man and has, on a longitudinal edge, a recess in the V notch to receive the attachment of the scrotum, and is composed of rigid, partially rigid or completely elastic soft material. All the disadvantages of previously known positioning aids are avoided by this testis support, which is also denoted a testis seating. Thus, in particular, the elevated testis of a recumbent man is prevented from slipping back. This elevation is necessary for more rapid and favourable healing of inflammatory diseases of testes and epididymides.

In contrast to a cloth affixed to the thighs, the testis support according to the invention can easily be removed and also re-attached by the patient himself.

If desired, the support can carry a layer of material. Therapeutic measures, such as poultices, application of ointments, powders or the like are made possible or facilitated by this means.

In a development of the invention, the support is affixed with tapes or bandages to the patient and, in a further development, it can be composed of several support parts which move against one another and are connected together in the manner of a hinge. By this means, the patient is made able to stand up and walk about even with the support in place.

An exemplary embodiment of the invention is represented in the drawing. In this:

Figure 1:
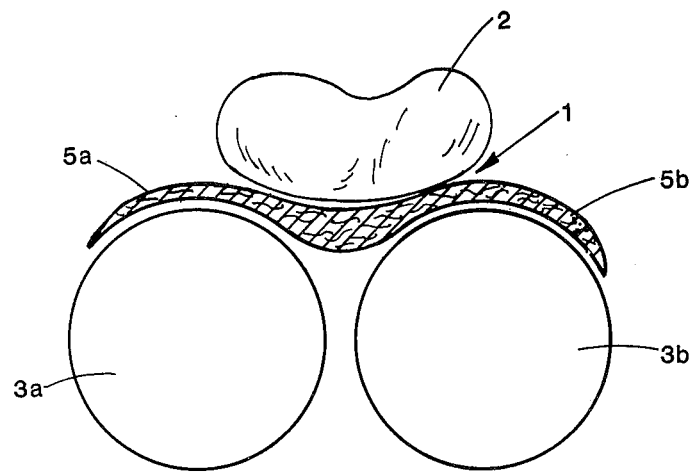
FIG. 1 shows a cross-section through the testis seating lying on the thighs.
Figure 2:
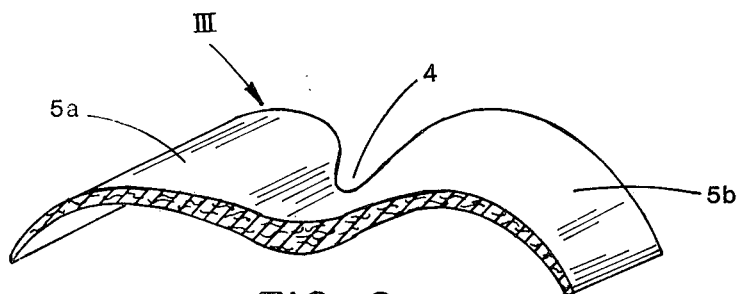
FIG. 2 shows a perspective view of the testis seating.

FIG. 1 represents a cross-section through the testis seating 1 lying on the thighs 3a and 3b. The testis seating has the form of a plane support 1 which, in its longitudinal axis, has a slight V-shaped deviation from planarity so that its wings 5a and 5b lie on and lightly grip the thighs 3a and 3b of the recumbent man. The perspective view of the testis seating 1 in FIG. 2 shows particularly clearly the slight V-shaped deviation from planarity of the support 1.

Figure 3:
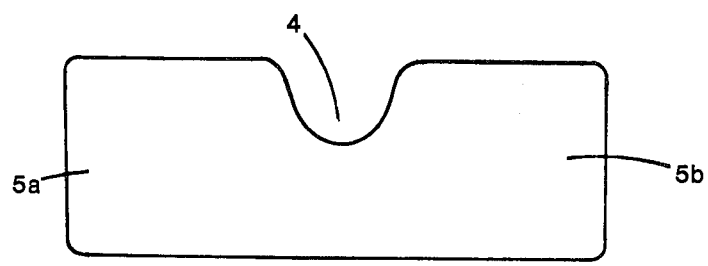
FIG. 3 shows a plan view of the testis seating from the direction of arrow III in FIG. 2
Figure 4:
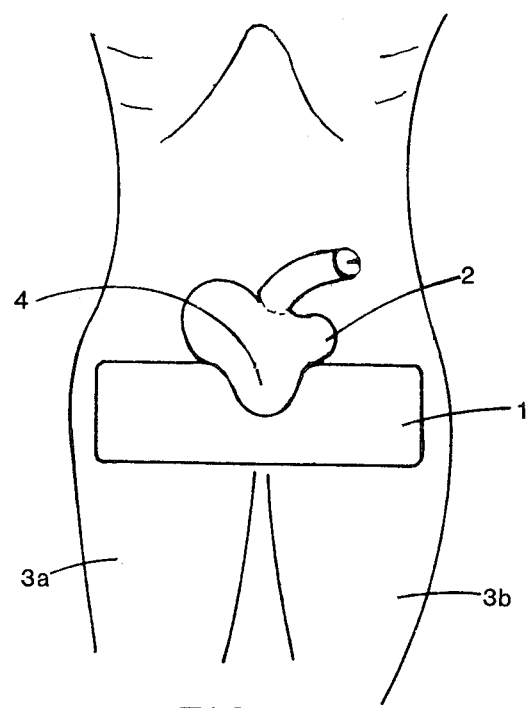
FIG. 4 shows a plan view of a recumbent patient with the testis seating in place.

The testis seating 1 has a recess 4 in the V notch on a longitudinal edge. The recess 4 is pushed around the attachment of the scrotum so that the scrotum 2 is brought to lie on top of the testis seating 1 and is thus elevated, as is shown in FIG. 1. A plan view of the support or testis seating 1 is again shown in FIG. 3. The use of the testis seating 1 is as follows: initially, the diseased scrotum 2 of the recumbent patient is pushed upwards and in the direction of the abdomen. The testis seating 1 is then placed on the thighs 3a and 3b and the recess 4 is advanced to the attachment of the scrotum. The scrotum 2 is then placed on the testis seating 1.

The testis seating or support 1 is preferably provided with a layer of material. The layer of material can have several useful properties: it can repel or absorb moisture, it can support wet dressings or can also serve as a support for medicaments.

In a development of the testis seating, it can be provided with tapes or bandages with which the seating can be affixed to the patient. It is also possible to make the testis seating or support from several support parts which move against one another and are connected together in the manner of a hinge. When a testis seating of this type, composed of several parts connected together by hinges, is additionally provided with tapes and/or bandages, then it is quite possible for the patient to move with this and, for example, stand up.

I claim:

1. An improved surgical testis support device for elevating and supporting for treatment the diseased testis and epididymides of a recumbant male, said device comprising:
   a generally rectangular seating member for positioning across the thighs of a male;
   said seating member being non planar and having curved wings at each end to generally conform to said thighs;
   a generally "V" shaped curved notch between said curved wings for location beneath the male testes; and
   a recess along one longitudinal edge of said seating member at said "V" shaped curved notch for accommodating and to underlie the male scrotum when said seating member is positioned to support said testes.

2. The testis support of claim 1, wherein the said recess has its largest longitudinal dimension at said edge and gradually reduces in dimension inwardly of said edge.

3. Testis support according to claim 1, characterised in that the support (1) has a layer of material.

4. The testis support of claim 1 further comprising means to fix the support to the patient.

5. The testis support of claim 3 further comprising means to fixe the support to the patient.

6. The testis support of claim 1, wherein the said curved wings of the seating member are concave downward to follow the contour of the thigh and the V-shaped curved notch is concave upward.

7. The testis support of claim 1 wherein the seating member is composed of a substantially rigid material with a cushioned covering.

* * * * *